United States Patent [19]

Wolf

[11] 4,220,611

[45] Sep. 2, 1980

[54] POLYOXYALKYLENE BRIDGED PHOSPHATE ESTERS

[75] Inventor: Harold P. Wolf, Whippany, N.J.

[73] Assignee: Sandoz, Inc., E. Hanover, N.J.

[21] Appl. No.: 920,368

[22] Filed: Jun. 29, 1978

[51] Int. Cl.$^2$ .................................................. C07F 9/08
[52] U.S. Cl. ...................... 260/929; 252/49.7; 252/49.8; 252/49.9; 252/94; 252/132; 252/173; 252/175; 252/351; 252/DIG. 13; 260/925; 260/928; 544/78; 546/255
[58] Field of Search ................ 260/925, 929, 297 P, 260/928; 544/78; 546/255

[56] References Cited

U.S. PATENT DOCUMENTS

| | | | |
|---|---|---|---|
| B 502,993 | 2/1976 | Shim | 260/929 |
| 2,411,671 | 11/1946 | Smith et al. | 260/928 |
| 2,736,737 | 2/1956 | Morris | 260/928 |
| 2,782,128 | 2/1957 | Paist et al. | 260/928 |
| 2,885,430 | 5/1959 | Scherer et al. | 260/929 |
| 2,909,559 | 10/1959 | Lanham | 260/928 |
| 2,974,066 | 3/1961 | Macura et al. | 260/925 |
| 3,429,824 | 2/1969 | Tate | 260/929 |
| 3,472,919 | 10/1969 | Nagy et al. | 260/929 |
| 3,767,732 | 10/1973 | Klose | 260/929 |
| 3,869,526 | 3/1975 | Combey et al. | 260/929 |
| 3,986,990 | 10/1976 | Giolito | 260/929 |
| 3,992,487 | 11/1976 | Shim | 260/929 |
| 4,010,145 | 3/1977 | Russen et al. | 528/280 |
| 4,056,480 | 11/1977 | Herber | 260/929 |
| 4,163,767 | 8/1979 | Giolito | 260/929 |

FOREIGN PATENT DOCUMENTS

1424513  2/1976  United Kingdom .................... 260/929

*Primary Examiner*—Mary C. Lee
*Attorney, Agent, or Firm*—Gerald D. Sharkin; Richard E. Vila; Joseph J. Borovian

[57] ABSTRACT

The invention relates to novel, polymeric phosphate esters containing at least two orthophosphate groups bridged by a polyoxyalkylene radical, and to the use of said esters as emulsifiers, surfactants, dispersants and fiber finishing agents.

12 Claims, No Drawings

POLYOXYALKYLENE BRIDGED PHOSPHATE ESTERS

This invention relates to a new class of organic phosphorus compounds. More particularly, it relates to novel, polymeric phosphate esters containing at least two orthophosphate groups bridged by a polyoxyalkylene radical and to the use of said esters as emulsifying agents, surface active agents, dispersing agents and fiber finishing agents.

It is well known in the art to employ phosphate esters to improve the properties of a wide variety of compositions. Moreover, it is also widely recognized that the phosphate ester compounds, per se, possess a wide range of utilities. For example, U.S. Pat. No. 2,411,671 is directed to compounds of the formula

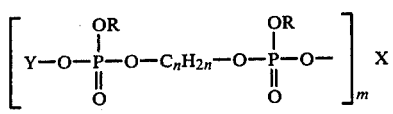

wherein R is $C_{1-18}$ alkyl; Y is alkyl or a monovalent metal; X is an organic ammonium group or a metal; m is an integer corresponding to the value of X; and n is an integer from 2 to 6, which compounds are useful as foam inhibitors in lubricating compositions. U.S. Pat. No. 2,736,737 discloses, inter alia, compounds of the formula

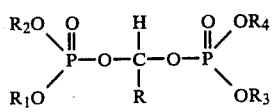

wherein R, $R_1$, $R_2$, $R_3$ and $R_4$ are H, unsubstituted and substituted aliphatic groups or unsubstituted and substituted aromatic groups, which compounds are useful as additives in lubricating compositions. U.S. Pat. No. 2,782,128 is directed to compounds of the formula

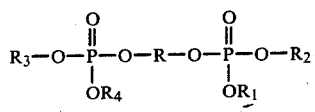

wherein R is a $C_2$–$C_{10}$ alkylene or monoxyalkylene radical, and $R_1$, $R_2$, $R_3$ and $R_4$ are $C_1$–$C_{10}$ alkyl, which compounds are useful as plasticizing agents in thermoplastic materials. U.S. Pat. No. 2,871,202 discloses, inter alia, compounds of the formula

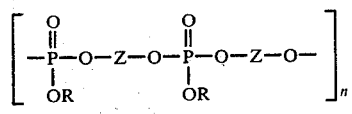

wherein R is $C_1$–$C_4$ alkyl; Z is a short chain alkylene radical; and n is an integer corresponding to the degree of polymerization, which compounds are useful as plasticizing agents and lubricant additives. U.S. Pat. No. 2,909,559 discloses compounds of the formula

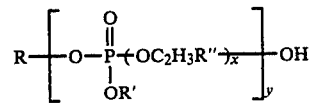

wherein R and R' are alkyl, haloalkyl, aryl, haloaryl or alkaryl; R" is H, methyl, ethyl or halomethyl; x is an integer from 1 to 10; and y is an integer from 2 to 10, which compounds are useful as lubricity agents, plasticizers, insecticides and flame-proofing agents. U.S. Pat. No. 3,380,927 is directed to phosphate co-esters of aliphatic alcohols and nonionic adducts of ethylene oxide and organic compounds containing reactive hydrogen atoms, which compounds possess a broad spectrum of surface active properties. U.S. Pat. No. 3,429,824 is directed to compounds of the formula

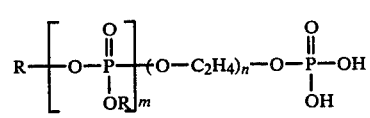

wherein R is hydrogen or a $C_{13}H_{27}O\text{-}(C_2H_4O)_{n-1}C_2H_4$ group in which n is an integer 1 to 3; m is an integer 2 or 3 and with the proviso that R is hydrogen not more than m minus one times, which compounds are useful in the prevention and/or inhibition of buildup of scale deposits in aqueous system. U.S. Pat. No. 3,869,526 is directed to compounds of the formula

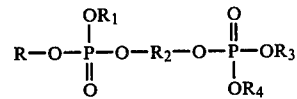

wherein R, $R_1$, $R_3$ and $R_4$ are $C_1$–$C_{15}$ alkyl, aryl or $C_6$–$C_{15}$ alkaryl; and $R_2$ is $C_2$–$C_6$ alkylene or a $C_4$–$C_{20}$ hydrocarbon ether residue, with the proviso that R, $R_1$, $R_3$ and $R_4$ are not all alkyl nor are they all aryl containing 6 to 8 carbon atoms, which compounds are useful as plasticizers.

Accordingly, it is an object of the present invention to provide improved organic phosphorus compounds. It is another object of the present invention to provide a novel class of phosphate ester compounds. It is still another object of the present invention to provide phosphate ester compounds which can be utilized in a wide variety of compositions. It is yet still another object of the present invention to provide phosphate ester compounds which can be incorporated in a wide variety of compositions to improve the properties of said compositions.

The attainment of the above objects is made possible by a compound or mixture of compounds of formula I:

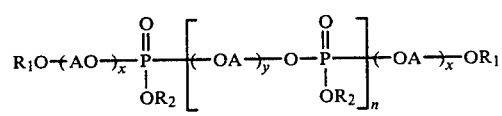

wherein
each $R_1$, independently, is the residue of a straight or branched chain $C_6$–$C_{22}$ fatty alcohol or the residue of a straight or branched chain mono- or dialkylphenol wherein the alkyl group of the mono- or the alkyl groups of the dialkylphenol contain from 6 to 12 carbon atoms, p1 each A, independently, is a divalent, aliphatic, straight or branched chain hydrocarbylene radical containing from 2 to 6 carbon atoms, each x, independently, is 0 or an integer 1 to 100, preferably an integer 1 to 100, y is an integer 2 to 30, n is an integer 1 to 3, and the $R_2$'s have the same significance and are hydrogen or a cation selected from the group consisting of alkali metal, alkaline earth metal, ammonium, mono-, di- and trialkanol ammonium wherein the alkanol group contains 2 to 4 carbon atoms, mono-, di-, tri- and tetraalkylammonium wherein the alkyl group contains 1 to 4 carbon atoms, pyridinium and morpholinium.

Preferred compounds of formula I are the compounds of formula Ia:

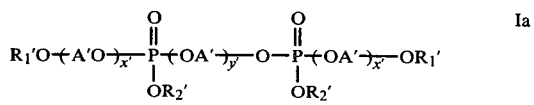

wherein
each $R_1'$, independently, is the residue of a straight or branched chain $C_8$–$C_{14}$ fatty alcohol or the residue of a straight or branched chain mono- or dialkylphenol wherein the alkyl group of the mono- or the alkyl groups of the dialkylphenol contain from 8 to 12 carbon atoms, each A, independently, is a divalent, straight or branched chain alkylene radical containing from 2 to 4 carbon atoms, each x', independently, is 0 or an integer 1 to 40, preferably an integer 1 to 40, y' is an integer 2 to 20, and the $R_2''$s have the same significance and are hydrogen or a cation selected from the group consisting of alkali metal, ammonium and mono-, di- and trialkanol ammonium wherein the alkanol group contains 2 to 4 carbon atoms, or a mixture of compounds of formula Ia.

Particularly preferred compounds of formula I are the compounds of formula Ib:

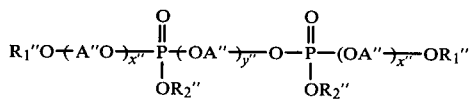

wherein
each $R_1''$, independently, is the residue of the straight or branched chain $C_{10}$–$C_{14}$ fatty alcohol or the residue of a straight or branched chain mono- or dialkylphenol wherein the alkyl group of the mono- or the alkyl groups of the dialkylphenol contain from 8 to 10 carbon atoms, each A'', independently, is ethylene or propylene, each x'', independently, is 0 or an integer 1 to 20, y'' is an integer 2 to 15, and the $R_2'''$s have the same significance and are hydrogen or a cation selected from sodium, potassium, ammonium or monoalkanol ammonium wherein the alkanol group contains 2 to 4 carbon atoms, or a mixture of compounds of formula Ib.

Most particularly preferred of the compounds of formula Ib are those compounds wherein A'' is ethylene and the terminal groups, i.e., the —$(OA'')_{x''}OR_1''$ groups, are identical, or a mixture of said compounds.

When $R_1$, $R_1'$ and $R_1''$ are residues of fatty alcohols, they are preferably alkyl groups, more preferably n-alkyl groups, having the indicated number of carbon atoms.

The compounds of formula I wherein n is 1 and the terminal groups —$(OA)_x OR_1$ are identical may be produced by a two-step reaction wherein a compound of formula II,

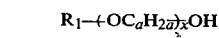

wherein $R_1$ and x are as defined in formula I and a is an integer 2 to 6, reacted with a phosphorylating agent, preferably phosphoryl chloride, under substantially anhydrous conditions at a temperature of −10°–100° C., preferably 0°–90° C., more preferably, 20°–70° C. in a molar ratio of 1:1 to produce a compound of formula III,

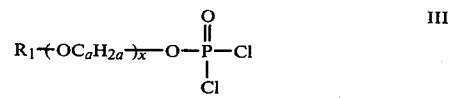

wherein $R_1$, a and x are as defined above. Preferably, the reaction mixture is swept by an inert atmosphere to displace the by-product, HCl.

As is well known to those skilled in the art, the reaction time necessary is inversely related to the reaction temperature, i.e., the higher the reaction temperature, the shorter the reaction time. It is, therefore, impossible to give a precise reaction time. However, a reaction time of 15 minutes —24 hours is generally acceptable with a reaction time of 30 minutes –20 hours being preferred.

Although the reaction is preferably conducted under substantially anhydrous conditions, an inert, organic solvent may be employed as a processing aid. Any inert, organic solvent which is adapted to dissolving the reactants and reaction product and has a boiling point at or above the desired reaction temperature may be used. Suitable solvents are known and available and include, by way of illustration, an aromatic solvent, e.g., benzene or toluene.

By the phrase "swept by an inert atmosphere" is meant purging the reaction with nitrogen, helium, neon, argon, krypton or xenon, or a mixture thereof.

The second step involves the reaction of a compound of formula III with a compound of formula IV,

wherein a is as defined above and b is an integer 2 to 30, in a molar ratio of 2:1. The reaction is carried out under substantially anhydrous conditions at a temperature of −10°−100° C., preferably 10°–70° C., more preferably 10° C. and is preferably swept by an inert atmosphere to displace the by-product, HCl. The resultant product is then hydrolyzed and, preferably, neutralized to produce the final ester product in salt form.

As in the case of the first step, a precise reaction time cannot be given because the higher the reaction temperature, the shorter the reaction time. However, a reaction time of 15 minutes - 4 days, preferably, 30 minutes—3 days, is generally employed.

Any inert, organic solvent in which the reactants are soluble and which has a boiling point at or above the desired reaction temperature may be employed as a processing aid.

The compounds of formula I wherein n is 1 and the terminal groups $-(OA)_{\overline{x}}OR_1$ are identical may also be produced by a two-step reaction wherein a compound of formula IV, as defined above, is reacted with a phosphorylating agent, preferably, phosphoryl chloride, in a molar ratio of phosphorylating agent to to compound of formula IV of 2:1 under the same reaction conditions described above with respect to the first step, hereinafter referred to as first-step reaction conditions, to obtain a phosphochloridate compound of formula V,

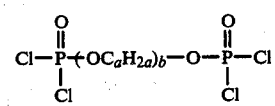

The second step involves the reaction of the phosphochloridate compound with a compound of formula II, as defined above, in a molar ratio of 1:2 under the same reaction conditions described above with respect to the second step, hereinafter referred to as second-step reaction conditions. The resultant product is then hydrolyzed and, preferably, neutralized to produce the final ester product in salt form.

The compounds of formula I wherein n is 1 and the terminal groups $-(OA)_{\overline{x}}OR_1$ are different may be produced by a stepwise reaction comprising reacting a compound of formula II, as defined above, with a phosphorylating agent, preferably phosphoryl chloride, in a molar ratio of 1:1 to produce a compound of formula III, as defined above under first-step reaction conditions. The second step involves the reaction of a compound of formula III with a compound of formula IV, as defined above, in a molar ratio of 1:1 to produce a compound of formula VI,

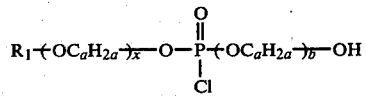

wherein $R_1$, a, b and x are as defined above, under second-step reaction conditions. The third step involves the reaction of a compound of formula VI with an equimolar amount of the phosphorylating agent employed above in the first step to produce a compound of formula VII,

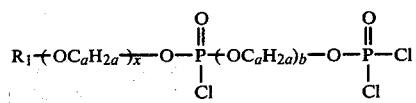

wherein $R_1$, a, b and x are as defined above. The final step involves the reaction of a compound of formula VII with an equimolar amount of a compound of formula II which is different from that employed in the first step. The resultant product is then hydrolyzed and, preferably, neutralized to produce the final ester product in salt form.

The third step is carried out under first-step reaction conditions, whereas the final step is carried out under second-step reaction conditions.

The compounds of formula I wherein n is 1 and the terminal groups $-(OA)_{\overline{x}}OR_1$ are different may also be produced by a two-step reaction wherein two different compounds of formula II, as defined above, are reacted with a phosphorylating agent, preferably phosphoryl chloride, in a molar ratio of phosphorylating agent to each of the compounds of formula II of 1:1 to produce two different compounds of formula III, as defined above, under first-step reaction conditions.

The second step involves the reaction of the compounds of formula III with a compound of formula IV, as defined above, in a molar ratio of 2:1 under second-step reaction conditions. The resultant product is then hydrolyzed and, preferably, neutralized to produce the final ester product in salt form.

The compounds of formula I wherein n is 2 may be produced by a step-wise reaction wherein the first three steps are identical to that described above regarding the process for preparing compounds of formula I wherein n is 1 and the terminal groups $-(OA)_{\overline{x}}OR_1$ are different. The fourth step involves the reaction of a compound of formula VII, as defined above, with an equimolar amount of a compound of formula IV, which may be the same or different from that employed in the second step, to produce a compound of formula VIII,

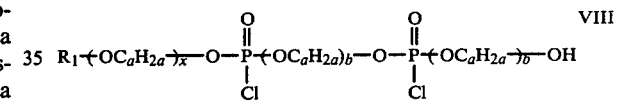

wherein $R_1$, a, b and x are as defined above. The fifth step involves the reaction of a compound of formula VIII with an equimolar amount of the phosphorylating agent employed in the first and third steps to produce a compound of formula IX,

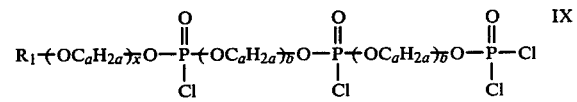

wherein $R_1$, a, b and x are as defined above. The reaction concludes with a final step involving the reaction of a compound of formula IX with an equimolar amount of a compound of formula II, which may be the same or different from that employed in the first step. The resultant product is then hydrolyzed and, preferably, neutralized to produce the final ester product in salt form.

The fourth and final steps are carried out under second-step reaction conditions, whereas the fifth step is carried out under first-step reaction conditions.

The compounds of formula I wherein n is 2 may also be produced by a two-step reaction wherein a compound of formula IV, as defined above, is reacted with a phosphorylating agent, preferably phosphoryl chloride, in a molar ratio of phosphorylating agent to a compound of formula IV of 1:2 under first-step reaction conditions to obtain a compound of formula X,

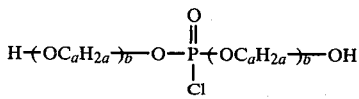

wherein a and b are as defined above.

Depending upon the ester product desired, the second step either involves the reaction of a compound of formula X, as described above, with a compound of formula III, as described above, in a molar ratio of 1:2, which results in a compound wherein the terminal groups $-(OA)_{\overline{x}}OR_1$ are identical, or involves the reaction of one mole of a compound of formula X, as described above, with one mole each of two different compounds of formula III, as described above, which results in a compound wherein the terminal groups $-(OA)_{\overline{x}}OR_1$ are different.

In either instance, the reaction is carried out under second-step reaction conditions. The resultant product is then hydrolyzed and, preferably, neutralized to produce the final ester product in salt form.

Where compounds of formula I wherein n is 3 are desired, either 2 moles of a compound of formula VII, as defined above, or 1 mole each of two different compounds of formula VII is reacted with 1 mole of a compound of formula IV under second-step reaction conditions. The resultant product is then hydrolyzed and, preferably, neutralized to produce the final ester product in salt form.

Although phosphoryl chloride is the preferred phosphorylating agent, the compounds of formula I may also be produced by gradually introducing phosphorus pentoxide to a mixture comprising at least one compound of formula II and a compound of formula IV in a proportion such that the total number of equivalents combiined of at least one compound of formula II and a compound of formula IV to the number of equivalents of phosphorylating agent, calculated as phosphorus pentoxide ($P_2O_5$), is within the range from about 1.5:1 to 3:1. The reaction is exothermic and the addition of the phosphorus pentoxide should be controlled as to prevent the temperature from rising to the boiling point of the mixture. In general, the reaction is conducted at a temperature range between 40° C. and 160° C., preferably between 50° C. and 100° C. Preferably, the reaction mixture is vigorously stirred during the addition of the phosphorus pentoxide to ensure a uniform and maximum rate of reaction within the controlled range of temperatures. When all of the phosphorus pentoxide has been added, the reaction mixture is held at the reaction temperature for at least an additional 60 minutes to ensure completeness of reaction. After cooling the resultant mixture to room temperature and separating out any unreacted phosphorus pentoxide, a mixture of compounds is obtained, predominant of which is the desired compound of formula I. In this connection, it is believed that the molecules of the compound(s) of formula II and the molecules of the compound of formula IV are linked together in the larger molecule through an intermediate orthophosphate bridge and that less than all of the orthophosphate protons are consumed by the ester bonds, so that chiefly monohydrogen orthophosphate and to a minor degree dihydrogen orthophosphate esters are obtained.

The compounds of formula II which are utilized in preparing the compounds of the instant invention represent a widely recognized class of compounds comprising fatty alcohols, mono- or dialkylphenols and the corresponding alkyleneoxy derivatives thereof, preferably, the ethyleneoxy derivatives. The fatty alcohol ethoxylates comprise the condensation product of aliphatic alcohols having from 6 to 22 carbon atoms, in either straight chain or branched chain configuration with ethyleneoxide, e.g., a tridecanol ethylene oxide condensation product having from 1 to 15 moles of ethylene oxide per mol of tridecanol. The mono- or dialkylphenol ethoxylates comprise the condensation product of a mono- or dialkylphenol wherein the alkyl group of the mono- or the alkyl groups of the dialkylphenol contains from 6 to 12 carbon atoms in either a straight or branched chain configuration with ethylene oxide, e.g., a nonylphenol ethylene oxide condensation product having from 8 to 25 moles of ethylene oxide per mole of nonylphenol, available commercially under the name Igepals. When not available commercially, the foregoing ethoxylates may be readily made by conventional reaction of ethylene oxide and the fatty alcohol or mono- or dialkylphenol compound. Generally speaking, anywhere from 1 to 100 moles, preferably 1 to 40 moles, of ethylene oxide may be reacted per mol of fatty alcohol or mono- or dialkylphenol, with the water solubility or dispersibility of the ethoxylate usually increasing as the number of moles of reacted ethylene oxide increases.

The compounds of formula IV which are also utilized in preparing the instant compounds are also well known and are most often referred to by those skilled in the art as "Polyalkylene ether glycols". They are sometimes known as polyalkylene glycols, polyalkylene oxide glycols, polyglycols or polyoxyalkylene diols. As indicated above, they may be represented by the formula $HO-(C_aH_{2a}O)_b H$. In the polyoxyalkylene diols useful in this invention, a is an integer 2 to 6, preferably 2 or 3 and b is an integer 2 to 30, preferably 2 to 20, the simplest of which is diethylene glycol. Certain of the compounds of formula IV are available under the commercial name Carbowax and prepared by the addition of ethylene oxide to ethylene glycol, e.g., Carbowax 300 contains on average 6.4 moles of ethylene oxide per mole of glycol and Carbowax 600 contains on average 13.2 moles of ethylene oxide per mole of glycol. The compounds of formula IV which are not available commercially may be prepared by the addition of an alkylene oxide to a low molecular weight glycol, e.g., ethylene glycol, diethylene glycol, triethylene glycol, etc. Not all the hydrocarbylene radicals present need be the same. Polyoxyalkylene diols formed by the copolymerization of a mixture of different alkylene oxides or glycols may be used or the polyoxyalkylene diol may be derived from a cyclic ether such as dioxolane, which results in a product having the formula,

The hydrocarbylene radicals may be straight chain or may have a branched chain as in the compound known as polypropylene ether glycol, which has the formula,

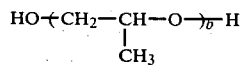

As indicated above, the product derived from each of the various processes described above is hydrolyzed and, preferably, neutralized to yield the final ester product in salt form.

The hydrolysis, i.e., the preparation of the compounds of formula I in free acid form, is effected under mild, basic conditions, preferably employing an alkali or alkaline earth metal hydroxide, more preferably, an alkali metal hydroxide, e.g., sodium or potassium hydroxide. The hydrolysis may be carried out conveniently at a temperature of from −10° to 60° C., preferably, 10° to 30° C.

Neutralization is conveniently effected employing an alkali or alkaline earth metal hydroxide, ammonium hydroxide or by reaction with a mono-, di-, or tri-($C_2$–$C_4$) alkanol ammonium compound, a mono-, di-, tri- or tetra-($C_1$–$C_4$) alkylammonium compound, pyridine or morpholine. The neutralization may be carried out conveniently at a temperature of from −10° to 90° C., preferably, 10° to 30° C.

The most conspicuous property of the compounds of formula I is their great activity at surfaces and interfaces, making them especially useful as emulsifiers, surfactants, dispersants and lubricants. As a result, the possible applications of these new compounds are extremely varied. For instance, they can be used as wetting, frothing or washing agents in the treating and refining of textiles; for converting liquid or solid substances which per se are insoluble in water (such as hydrocarbons, higher alcohols, oils, fats, waxes and resins) into creamy emulsions, clear solutions or fine, stable dispersions; for carbonizing; for dyeing, e.g., in the pasting of dyestuffs, in dyeing acetate with insoluble dyestuffs, in the preparation of dyestuffs in finely divided form, etc.; for fulling, sizing, impregnating and bleaching treatments; as cleansing agents in hard water; in tanning and mordanting processes; as a means for improving the absorptive power of fibrous bodies; and as an aid in softening baths for hides and skins.

In addition, these compounds are valuable emulsifiers for insecticide compositions and agricultural spray such as DDT, 2,4-D, dormant or mineral oil sprays, nicotine sulfate, and the like.

These compounds are valuable for use as additives to petroleum products, as additives for fuel oils, hydraulic fluids, lubricating oils, cutting oils and greases; and as additives to the water or brine used for oil recovery from oil-bearing strata by flooding techniques.

Other valuable uses are in metal cleaning compositions and dry cleaning compositions; as additives for rubber latices; as additives to plasticizers and modifiers for vinyl plastics, alkyd resins, phenol-formaldehyde resins, and other types of polymeric-type plastic materials; for incorporation into adhesives, paint, linoleum and the like; for use in bonding agents used in various insulating and bulking materials; as refining aids in wood digesters to prepare pulp; as additives to pulp slurries in beating operations to prevent foaming and also to aid the beating operation in papermaking; and for use in dishwashing compositions.

These compounds are also useful as emulsifiers for emulsion polymerization; as plasticizers, mercerizing assistants, dispersing agents, softening agents, lime-soap dispersants and anti-static agents.

They are valuable as anti-fogging agents for use on glass and other surfaces where the accumulation of an aqueous fog is detrimental; and are useful in the rayon industry as additives to the dope or to the spinning bath and as aids in clarifying viscose rayon.

These compounds are valuable in the preparation of skin creams, lotions, salves and other cosmetic preparations such as hair-waving sets, shampoos, toothpastes, etc. They are also of value in food products as foaming agents, emulsifying agents and softening agents.

The compounds of the invention also find use in primary spin finishes, oversprays and in binding oils for processing natural and man-made fibers. They are also useful for improving the de-inking effect in recycling paper and for the prevention of silicate-scale build-up on textile, detergent processing equipment.

The compounds of this invention may also advantageously be employed in detergent compositions containing an anionic, nonionic, ampholytic or zwitterionic surfactant, or mixtures thereof, and/or builders and the like. As representative of anionic surfactants may be mentioned: (1) alkylbenzenesulfonates, such as sodium and potassium salts having a branched or straight chain alkyl portion of about 9 to about 15 carbon atoms; (2) alkyl sulfates, such as the sodium and triethanolammonium salts of $C_{10}$–$C_{20}$ alkyl sulfuric acid, prepared by sulfating the alcohols derived from coconut oil or tallow, or prepared synthetically; (3) the alkali metal and ammonium salts of the sulfated ethoxylates of a long-chain alcohol and 3 to 5 molar proportions of ethylene oxide, e.g., the ammonium salt of an ethoxylate containing an average of 3.1 molar proportions of ethylene oxide and 1 mole of an alcohol mixture known commercially as ALFOL 1412, composed of about ⅔ n-tetradecanol and about ⅓ n-dodecanol; (4) the compounds known as "Medialans" which are amido carboxylic acids formed by condensing fatty acids of $C_8$–$C_{22}$ chain length with sarcosine, $CH_3NHCH_2COOH$; (5) alkanesulfonates, such as ammonium dodecanesulfonate; (6) alkoxyhydroxypropanesulfonates, such as the water-soluble salts of 3-dodecyloxy-2-hydroxy-1-propane-sulfonate; (7) soaps, the surface-active substances formed usually by the reaction of caustic alkalies with natural glyceridic fats and oils, generally prepared in high purity, and having the generic molecular formula RCOONa, wherein R is a straight-chain hydrocarbon group having from about 7 to about 21 carbon atoms; and (8) olefin sulfonates, such as dodecene sulfonate, and the compounds described in U.S. Pat. No. 3,332,880. As representative of nonionic surfactants may be mentioned: (1) the Pluronics, formed by condensing propylene oxide with propylene glycol to a molecular weight of about 600 to 2500 to form a base followed by condensing ethylene oxide to this base to the extent of about 10 to about 90 percent, total molecule basis. U.S. Pat. No. 2,674,619 and U.S. Pat. No. 2,677,700 decribe operable compounds; (2) compounds formed by the simultaneous polymerization of propylene oxide and ethylene oxide, and containing randomly positioned oxypropylene and oxyethylene groups. These and related compounds are described in U.S. Pat. No. 2,979,528, U.S. Pat. No. 3,036,118, U.S. Pat. No. 3,022,335, U.S. Pat. No. 3,036,130 and U.S. Pat. No. 3,048,548; (3) alkyl phenols having 9 to 12 carbon atoms in the alkyl portion (straight or branched) ethoxylated with 4–10 molar proportions of ethylene oxide; and (4) ethoxylates of fatty alcohols having 8 to 18 carbon atoms per molecule and 5–30 molar proportions of oxyethylene groups.

As an example of an ampholytic surfactant may be mentioned the hydroxyalkyl methyl taurates, while cocodimethyl sulfopropyl betaine is exemplary of a zwitterionic surfactant.

Other common components of detergent compositions include alkaline builders such as the alkali metal salts of ortho-, meta-, poly- and pyro-phosphoric acids, including sodium hexametaphosphate, sodium pyrophosphate, trisodium phosphate, sodium tripolyphosphate, and the like, in addition to water-soluble derivatives of high polyoses such as sodium carboxymethyl cellulose, and other water-soluble salts for adjustment of pH, buffering, and the like such as sodium carbonate, sodium sesquicarbonate, sodium bicarbonate, sodium chloride, sodium sulfate, sodium bisulfate, sodium metasilicate, and the like.

The following examples, illustrating the novel phosphate esters of this invention, are presented without any intention that the invention be limited thereto. All parts and percentages are by weight.

EXAMPLE 1

To a reaction vessel containing 15.35 g. (0.1 moles) of phosphoryl chloride is added, with agitation over a period of 35 minutes at 20° C., 33.40 g. (0.1 moles) of TDA-3, a tridecanol condensed with 3 moles of ethylene oxide and available commercially from Emery Industries. Under constant agitation, the reaction mixture is purged with nitrogen overnight, while the temperature is maintained at 20° C. To the reaction mixture is added, with agitation over a period of 20 minutes at 20° C., 5.3 g. (0.05 moles) of diethylene glycol, after which time the reaction is allowed to continue for an additional 90 minutes. The resultant reaction mixture is then adjusted to a pH of 8 with aqueous potassium hydroxide and the crude product is then tray dried. After desalting by dissolution in methylene chloride, the residue is filtered and the methylene chloride is stripped to yield a viscous, clear, yellow liquid of the formula,

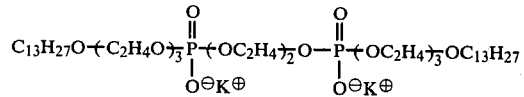

(a) Following essentially the above-described procedure, and instead of adding to the resultant reaction mixture a sufficient amount of aqueous potassium hydroxide to adjust the pH to 8, there is added one equivalent of potassium hydroxide (based on P), the free acid form of the above compound is obtained.

Upon treating the free acid form of the above compound with one equivalent (based on P) of:
 (b) ammonium hydroxide; or
 (c) monoethanolamine
there is obtained, the corresponding
 (b) ammonium salt (a viscous, translucent, amber liquid); and
 (c) monoethanolammonium salt, respectively.

EXAMPLE 2

To a reaction vessel containing 15.35 g. (0.1 moles) of phosphoryl chloride is added, with agitation over a period of 20-25 minutes at 20° C., 15 g. (0.95 moles) of Carbowax ® 300, an ethylene glycol containing 6.4 moles of ethylene oxide per mole of glycol. Under constant agitation, the reaction mixture is purged with nitrogen overnight, while the temperature is maintained at 20° C. To the reaction mixture is added, with agitation over a period of 20 minutes at 20° C., 20.2 g. (0.10 moles) of tridecanol. After the viscosity of the resultant reaction mixture is reduced by the addition of 20 ml. of tetrahydrofuran, the reaction mixture, under constant stirring at 20° C., is purged with nitrogen. After the reaction is allowed to continue for an additional 90 minutes, two portions of aqueous potassium hydroxide (100 meq., based on P) is added successively to the reaction mixture under constant stirring, while the temperature is maintained at 20° C. The resultant reaction mixture is then adjusted to a pH of 8 with an additional amount of aqueous potassium hydroxide and the crude product is then tray dried. After desalting by dissolution in methylene chloride, the residue is filtered and the methylene chloride is stripped to yield a viscous, translucent, pale yellow liquid of the formula,

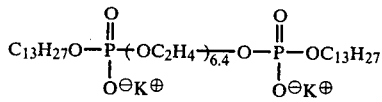

The product is a mixture of compounds having an average of 6.4 —OC$_2$H$_4$— radicals between the two phosphorus atoms.

Following essentially the above-described procedure, and instead of adding to the reaction mixture two successive portions of aqueous potassium hydroxide, there is added one equivalent (based on P) of 40% sodium hydroxide followed by an equivalent amount of:
 (a) triethanolamine;
 (b) monoethanolamine;
 (c) diisopropylamine;
 (d) sodium hydroxide; or
 (e) diethanolamine
there is obtained, the corresponding
 (a) triethanolammonium salt (a translucent, colorless gel);
 (b) monoethanolammonium salt (a viscous, translucent yellow liquid);
 (c) diisopropylammonium salt (a viscous, clear, yellow liquid);
 (d) sodium salt (a translucent, colorless gel); and
 (e) diethanolammonium salt (a viscous, translucent, pale yellow liquid), respectively.

EXAMPLE 3

Following essentially the initial procedure of Example 1, and using in place of diethylene glycol in the second step, an equivalent amount of Carbowax ® 300, there is obtained a viscous, slightly cloudy, yellow liquid of the formula,

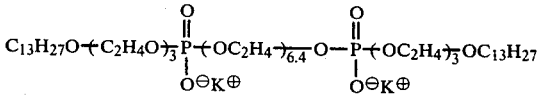

The product is a mixture of compounds having an average of 6.4 —OC$_2$H$_4$— radicals between the two phosphorus atoms.

EXAMPLE 4

Following essentially the initial procedure of Example 1, and using in place of TDA-3 in the first step, an equivalent amount of tridecanol, and using in place of diethylene glycol in the second step, an equivalent amount of Carbowax ® 600, an ethylene glycol containing 13.2 moles of ethylene oxide per mol of glycol, there is obtained a glassy to very viscous, clear, pale yellow liquid of the formula,

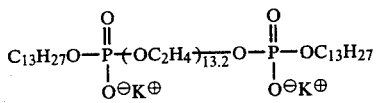

The product is a mixture of compounds having an average of 13.2 —OC$_2$H$_4$— radicals between the two phosphorus atoms.

Following essentially the remaining procedure of Example 1, there is obtained the corresponding
(a) free acid;
(b) ammonium salt (a viscous, translucent, pale yellow liquid); and
(c) monoethanolammonium salt, respectively.

EXAMPLE 5

Following essentially the initial procedure of Example 1, and using in place of TDA-3 in the first step, an equivalent amount of Trylox ® TDA-6, a tridecanol condensed with 6 moles of ethylene oxide, there is obtained a viscous, clear, colorless liquid of the formula,

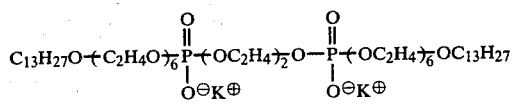

EXAMPLE 6

Following essentially the initial procedure of Example 1, and using in place of TDA-3 in the first step, an equivalent amount of Trylox ® TDA-6, and using in place of diethylene glycol in the second step, an equivalent amount of Carbowax ® 600, there is obtained a highly viscous, opaque, off-white liquid of the formula,

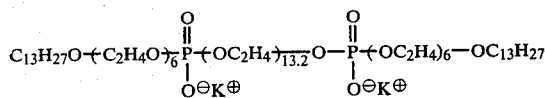

The product is a mixture of compounds having an average of 13.2 —OC$_2$H$_4$— radicals between the two phosphorus atoms.

EXAMPLE 7

To a reaction vessel containing 15.35 g. (0.1 moles) of phosphoryl chloride is added, with agitation over a period of 20-25 minutes at 12° C., 20.2 g. (0.1 moles) of tridecanol. Under constant agitation, the reaction mixture is purged with nitrogen overnight, while the temperature is maintained at 12° C. To the reaction mixture is added, with agitation over a period of 20 minutes at 12° C., 10.6 g. (0.1 moles) of diethylene glycol, after which time the reaction is allowed to continue for an additional 90 minutes. To the resultant reaction mixture is added, with agitation over a period of 20-25 minutes at 12° C., 15.35 g. of phosphoryl chloride. Under constant agitation, this reaction mixture is purged with nitrogen overnight, while the temperature is maintained at 12° C. To this mixture is added, with agitation over a period of 20 minutes at 12° C., 10.2 g. (0.1 moles) of 1-hexanol, after which time the reaction is allowed to continue for an additional 90 minutes. The resultant reaction mixture is then adjusted to a pH of 7 with aqueous potassium hydroxide and dried. After desalting by dissolution in methylene chloride, the residue is filtered and the methylene chloride is stripped to yield a viscous, translucent, colorless liquid of the formula,

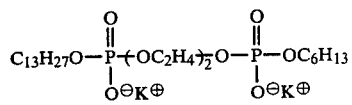

(a) Following essentially the above-described procedure, and instead of adding to the resultant reaction mixture a sufficient amount of aqueous potassium hydroxide to adjust the pH to 7, there is added one equivalent of potassium hydroxide (based on P), the free acid form of the above compound is obtained.

(b) Upon treating the free acid form of the above compound with one equivalent (based on P) of monoethanolamine, there is obtained the corresponding monoethanolammonium salt.

EXAMPLE 8

Following essentially the initial procedure of Example 1, and using in place of TDA-3 in the first step, an equivalent amount of Chemal ® DA-6, a decyl alcohol condensed with 6 moles of ethylene oxide, and using in place of diethylene glycol in the second step, an equivalent amount of Carbowax ® 300, there is obtained a viscous, nearly clear, colorless liquid of the formula,

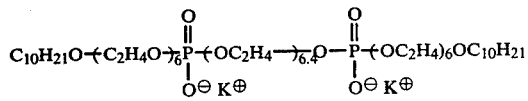

The product is a mixture of compounds having an average of 6.4 —OC$_2$H$_4$— radicals between the two phosphorus atoms.

Following essentially procedures (a) and (c) with respect to Example 1, there is obtained, the corresponding
(a) free acid; and
(b) monoethanolammonium salt, respectively.

EXAMPLE 9

Following essentially the initial procedure of Example 1, and using in place of TDA-3 in the first step, an equivalent amount of TL-974, a decyl alcohol condensed with 3 moles of ethylene oxide and available commercially from ICI America, and using in place of diethylene glycol in the second step, an equivalent amount of Carbowax ® 300, there is obtained a viscous, translucent, colorless liquid of the formula,

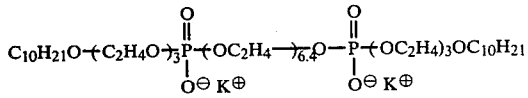

The product is a mixture of compounds having an average of 6.4 —OC$_2$H$_4$— radicals between the two phosphorus atoms.

EXAMPLE 10

To a reaction vessel containing 115.25 g. (0.75 moles) of phosphoryl chloride is added, with agitation over a period of 20-25 minutes at a temperature between 25° C. and 27° C., a mixture containing 48.8 g. (0.375 moles) of 2-ethylhexanol and 231.3 g. (0.375 moles) of Igepal ® CO-630, a nonylphenol condensed with 9 moles of ethylene oxide. Under constant agitation, the reaction mixture is purged with nitrogen overnight, while the temperature is maintained at between 25° C. and 27° C. To the reaction mixture is added, with agitation over a period of 2 hours at a temperature between 25° C. and 27° C., 112.5 g. (0.375 moles) of Carbowax ® 300, after which time the reaction is allowed to continue for an additional 18 hours. The resultant reaction mixture is then adjusted to a pH of 8 with aqueous potassium hydroxide and dried. After desalting by dissolution in methylene chloride, the residue is filtered and the methylene chloride is stripped to yield a viscous, clear, colorless liquid of the formula,

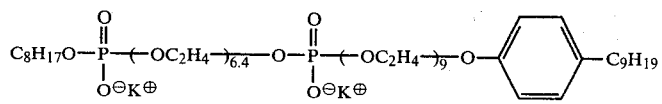

The product is a mixture of compounds having an average of 6.4 —OC₂H₄— radicals between the two phosphorus atoms.

EXAMPLE 11

To a reaction vessel containing 115.25 g. (0.75 moles) of phosphoryl chloride is added, with agitation over a period of 20-25 minutes at a temperature between 20° C., 289.45 g. (0.73 moles) of Igepal ® CO-430, a nonylphenol condensed with 3 moles of ethylene oxide. Under constant agitation, the reaction mixture is purged with nitrogen overnight, while the temperature is maintained at 23° C. To the reaction mixture is added with agitation at a temperature of 23° C., 109.5 g. (0.365 moles) of Carbowax ® 300 and the reaction is allowed to continue at this temperature for 40 hours, after which time the reaction is allowed to continue for an additional 6 hours at a temperature of 35° C. The resultant reaction mixture is then adjusted to a pH of 7.2 with aqueous potassium hydroxide and dried. After desalting by dissolution in methylene chloride, the residue is filtered and the methylene chloride is stripped to yield a translucent, colorless gel of the formula,

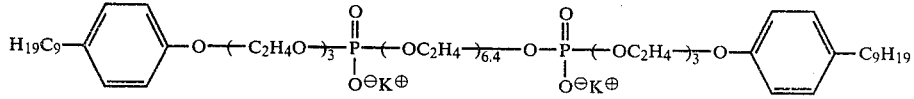

The product is a mixture of compounds having an average of 6.4 —OC₂H₄— radicals between the two phosphorus atoms.

Following essentially the above-described procedure, and instead of adding to the resultant reaction mixture a sufficient amount of aqueous potassium hydroxide to adjust the pH to 7.2, there is added one equivalent of potassium hydroxide (based on P) followed by one equivalent of:

(a) ammonium hydroxide; or
(b) monoethanolamine there is obtained, the corresponding (a) ammonium salt; and
(b) monoethanolammonium salt (a high viscosity, translucent, pale yellow liquid), respectively.

EXAMPLE 12

To a reaction vessel containing 76.75 g. (0.5 moles) of phosphoryl chloride is added, with agitation at a temperature between 0° C. and 5° C., 99.0 g. (0.494 moles) of tridecanol, after which time the reaction is allowed to continue for 6 hours while the temperature is maintained at between 0° C. and 5° C. To the reaction mixture is added, under constant agitation, 81.76 g. (0.247 moles) of DEG 3/2, a diethylene glycol to which is added 3 moles of propylene oxide and 2 moles of ethylene oxide, and the reaction is allowed to continue, under constant agitation, for 71.5 hours, during which time the temperature is very slowly increased to a final temperature of 35° C. The resultant reaction mixture is then adjusted to a pH of 7.5 with aqueous potassium hydroxide and the crude product is then dried under vacuum. After desalting by dissolution in methylene chloride, the residue is filtered and the methylene chloride is stripped to yield a viscous, translucent, pale yellow liquid of the formula,

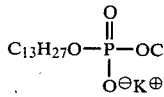 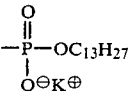

$$C_{13}H_{27}O-\overset{O}{\underset{O^\ominus K^\oplus}{P}}-OC_2H_4-O-(C_3H_6O)_{\overline{2}}-(C_2H_4O)_{\overline{2}}-C_3H_6OC_2H_4O-\overset{O}{\underset{O^\ominus K^\oplus}{P}}-OC_{13}H_{27}$$

EXAMPLE 13

To a reaction vessel containing a stirred mixture of 80.88 g. (0.4 moles) of tridecanol and 21.25 (0.2 moles) of diethylene glycol under a nitrogen sweep at a temperature of 50° C. is added, portionwise over a period of between 1½ and 2 hours, 23.38 g. (0.2 moles) of phosphorus pentoxide, the addition taking place under constant stirring while the temperature is slowly increased to 80° C. After the temperature is decreased to 50° C., the reaction is allowed to continue for an additional 20 hours, after which time the temperature is successively elevated to 100° C. for 15 minutes, 115° C. for 15 minutes, 125° C. for 15 minutes, 135° C. for 2 hours, 145° C. for 30 minutes and finally, 150° C. for 2 hours. After cooling to 20° C., the resultant reaction mixture is then adjusted to a pH of 7.5 with aqueous potassium hydroxide and the crude product is then dried under vacuum. After desalting by dissolution in methylene chloride, the residue is filtered and the methylene chloride is stripped to yield a viscous, translucent, brownish yellow liquid comprising a mixture of compounds, predominant of which is a compound of the formula,

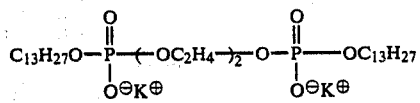

EXAMPLE 14

Severl representative compounds of the present invention were evaluated as wetting agents in accordance with the Draves Wetting Test (AATCC Test Method 17-1974) employing 5 g. cotton skeins and a 3 g. hook. The results of this evaluation appear in Tables 1 and 2 below.

Table 1

| Conc. | Ex. 1 | Ex. 2 | [1]Ex. 3 | Ex. 4 | Ex. 5 | [1]Ex. 6 | Ex. 7 |
|---|---|---|---|---|---|---|---|
| (g./l.) | Wetting Time, Seconds, in Distilled Water at R.T. | | | | | | |
| .61 | >200 | >200 | >200 | >200 | >200 | >200 | >200 |
| 1.25 | 135 | 105 | >200 | 90 | >200 | >200 | 105 |
| 2.50 | 70 | 32 | 80 | 32 | 165 | 175 | 27 |
| 5.00 | 43 | 19 | 39 | 15 | 80 | 90 | 8 |
| 10.00 | — | — | — | — | — | — | 2.7 |

| Conc. | Ex. 8 | Ex. 9 | Ex. 10 | Ex. 4b | Ex. 11 | Ex. 11b | [2]Strodex Super V-8 |
|---|---|---|---|---|---|---|---|
| (g./l.) | Wetting Time, Seconds, in Distilled Water at R.T. | | | | | | |
| .61 | >200 | >200 | >200 | >200 | >200 | >200 | 56 |
| 1.25 | >200 | >200 | >200 | >200 | >200 | >200 | 22 |
| 2.50 | >200 | 77 | >200 | 130 | >200 | >200 | 10 |
| 5.00 | 56 | 34 | 115 | 31 | 180 | >180 | 4.6 |
| 10.00 | 10 | — | — | 67 | — | and | |

[1]Example 3 and Example 6 were unstable in 8% NaOH.
[2]An alkoxylated monophosphate co-ester available commercially from Dexter Chemical.

Table 2

| Conc. | Ex. 1 | Ex. 2 | Ex. 4 | Ex. 5 | Ex. 8 | Ex. 9 |
|---|---|---|---|---|---|---|
| (g./l.) | Wetting Time, Seconds, in 8% NaOH at R.T. | | | | | |
| .62 | >200 | 165 | >200 | >200 | >200 | >200 |
| 1.25 | >200 | 54 | >200 | >200 | 73 | 50 |
| 2.50 | 140 | 27 | 85 | 115 | 40 | 22 |
| 5.00 | 66 | 14 | 44 | 73 | 24 | 13 |

| Conc. | Ex. 10 | Ex. 11 | Strodex Super V-8 |
|---|---|---|---|
| (g./l.) | Wetting Time, Seconds, in 8% NaOH at R.T. | | |
| .62 | >200 | >200 | 130 |
| 1.25 | >200 | >200 | 50 |
| 2.50 | 75 | >200 | 19 |
| 5.00 | 32 | 148 | 13 |

EXAMPLE 15

Several representative compounds of the present invention were evaluated as foaming agents according to the following procedure:

Into a glass stoppered 500 cc. graduated cylinder is added 200 cc. of water and 1 cc. (conc.-5 g./l.) of the compound which is being evaluated as a foaming agent. After the cylinder is stoppered, it is held horizontally and shaken in the horizontal position for 5 cycles (10 times). After the shaking is completed, the cylinder is set on the bench and the stopper is removed. The average height of foam is then recorded (initial). As a measure of foam stability, the average height of foam is recorded after 1 minute and 5 minutes has elapsed.

The test is repeated employing 2.5 g./l. and 1.25 g./l. of the test compound. The results of this evaluation appear in Table 3 below.

Table 3

| | 5 g./l. | 2.5 g./l. | 1.25 g./l. |
|---|---|---|---|
| Test Compound | Volume: initial/1 min./5 min.; 200 = no foam | | |
| Ex. 1 | 430/430/410 | 365/360/355 | 340/335/325 |
| Ex. 2 | 450/425/265 | 410/390/295 | 350/340/265 |
| Ex. 3 | 415/410/370 | 400/400/395 | 410/405/400 |
| Ex. 4 | 410/390/300 | 385/340/300 | 355/315/300 |
| Ex. 5 | 425/415/270 | 365/360/250 | 370/365/240 |
| Ex. 6 | 400/375/240 | 355/275/240 | 350/345/230 |
| Ex. 8 | 425/400/250 | 400/385/275 | 325/320/290 |
| Ex. 9 | 350/310/250 | 325/270/250 | 300/230/225 |
| Ex. 10 | 400/385/250 | 380/370/240 | 325/320/250 |
| Ex. 4b | 385/370/270 | 340/300/265 | 305/270/265 |
| Ex. 11 | 290/215/210 | 285/215/210 | 275/210/210 |
| Ex. 11b | 310/215/215 | 300/220/215 | 300/225/220 |
| Strodex Super V-8 | 530/530/400 | 475/470/450 | 490/485/475 |

EXAMPLE 16

Several representative compounds of the present invention were evaluated as dispersing agents by their ability to disperse sodium silicate according to the following procedure:

To a mixture containing 80 cc. of a[3]silicate stock solution and 10 cc. of the compound which is being evaluated as a dispersant is added 10 cc. of a[4]precipitate stock solution. After the resultant mixture is allowed to stand for 5 min., it is heated to boiling with occasional stirring and then filtered under vacuum through Whitman #29 filter paper. The results of this evaluation appear in Table 4 below.

[3]silicate stock solution—10 g. of sodium silicate and 2 g. of NaOH dissolved in 788 cc. of deionized water.
[4]precipitate stock solution—2.5 g. of $CaCl_2$ and 5.3 g. of $MgCl_2$ dissolved in water and diluted to 1000 mil.

Table 4

| Test Compound | Subjective description of a series of 2 or 3 tests |
|---|---|
| blank | medium-heavy precipitation |
| Ex. 1 | medium-heavy precipitation |
| Ex. 2 | light-medium precipitation |
| Ex. 3 | light-medium precipitation |
| Ex. 4 | light-medium precipitation |
| Ex. 5 | heavy precipitation |
| Ex. 6 | medium-heavy precipitation |
| Ex. 8 | medium-heavy precipitation |
| Ex. 9 | medium-heavy precipitation |
| Ex. 10 | medium precipitation |
| Ex. 11 | very light precipitation |

Table 4-continued

| Test Compound | Subjective description of a series of 2 or 3 tests |
|---|---|
| [5]DTC-100 | medium-heavy precipitation |
| Strodex Super V-8 | very light precipitation |

[5]a carboxymethylated polyoxyethylenated tridecanol detergent available commercially from Sandoz, Inc.

EXAMPLE 17

Several representative compounds of the present invention were also evaluated as dispersing agents by their ability to disperse titanium dioxide according to the following procedure:

To 50 g. of [6]TITANOX-RA NC in a beaker is added, sufficient water to form a stiff, slightly moist paste. This paste is Mix A, the system for which the Fluidity Point (amount of dispersant needed for initial dispersion) and the Concentration-Aggregation (C-A) Value (amount of dispersant needed to ensure that flocculation does not occur) is determined. The compound which is being evaluated as a dispersant is then added to Mix A in small increments with thorough but gentle mixing, until the pigment mass becomes fluid enough so that a spatula drawn through the mixture leaves no trail behind it. This system is Mix B. The concentration of dispersant added on a percent solids basis is the Fluidity Point. The pigment is now deflocculated and considered dispersed.

To 1 g. of [7]ACRYSOL GS is added 1 to 2 drops of Mix B and, after severe flocculation of the pigment system is noted, dropwise addition of Mix B is continued until the dispersed pigment absence of flocculation. The total amount of dispersant required to reach this point is recorded on a percent solids bases as the C-A value. The results of this evaluation appear in Table 5 below.

[6]a commercially available titanium dioxide pigment.
[7]an acrylic thickener available commercially from Rohm and Haas Company.

Table 5

| Test Compound | g. of experimental dispersant (based on 100% active solids) |
|---|---|
| Ex. 1 | 1.3 |
| Ex. 2 | 2.6 |
| Ex. 3 | 3.0 |
| Ex. 4 | 1.8 |
| Ex. 5 | 3.5 |
| Ex. 6 | 3.0 |
| Ex. 7 | 2.3 |
| Ex. 8 | 3.7 |
| Ex. 9 | 4.0 |
| Ex. 10 | 4.3 |
| Ex. 11 | 3.5 |
| Ex. 11b | 3.0 |
| Strodex Super V-8 | 2.5 |
| [8]Tamol L Conc | 2.5 |
| [9]Emcol PS-222 | 4.5 |
| [9]Emcol PS-413 | >10 |
| [9]Emcol CS-141 | 1.5 |

[8]a naphthalene sulfonate formaldehyde condensate dispersant available commercially from Rohm and Haas Company.
[9]an alkoxylated monophosphate co-ester available commercially from Witco Chemical Company.

EXAMPLE 18

Several representative compounds of the present invention were evaluated as detergents according to the following procedure:

Two solutions, one containing 25.0 g./l. of caustic flakes (as a control) and the other containing 25.0 g./l. of caustic flakes and 0.25 g. of the compound which is being evaluated as a detergent, are heated to boiling, after which time a cotton greige good swatch (1 $\frac{3}{4}''\times\frac{1}{4}''$) is added to each solution. After 1 hour at a boil, the swatches are rinsed at boiling temperature, neutralized at room temperature and rinsed again at a boil. After the swatches are extracted and dried, they are suspended at room temperature for 5 minutes in a solution containing 1 g./500 cc. of [10]AZO Rhodine 2G Conc. after which time they are allowed to air dry in a vertical position. The amount of dye absorbed by the swatches, i.e., the creep or crawl of the dye, is then measured; the greater the creep, the better the detersive ability of the test compound. The results of this evaluation appear in Tables 6, 6A and 6B below.

[10]commercially available red dye.

TABLE 6

| Test Compound | Absorbency (cm.) |
|---|---|
| Ex. 1 | 5.78 |
| Ex. 2 | 6.83 |
| Ex. 3 | 7.43 |
| Ex. 4 | 6.27 |
| Ex. 5 | 6.64 |
| Ex. 6 | 8.00 |
| Ex. 7 | 2.48 |
| DTC-100 | 6.93 |
| Strodex Super V-8 | 5.04 |

TABLE 6A

| Test Compound | Absorbency (cm.) |
|---|---|
| Ex. 2 | 8.20 |
| Ex. 4 | 6.50 |
| Ex. 8 | 7.80 |
| Ex. 9 | 6.50 |
| Strodex Super V-8 | 5.45 |

TABLE 6B

| Test Compound | Absorbency (cm.) |
|---|---|
| Ex. 10 | 6.95 |
| Ex. 11 | 6.55 |
| Ex. 11b | 7.15 |
| DTC-100 | 6.75 |
| Strodex Super V-8 | 5.05 |

EXAMPLE 19

Several representative compounds of the present invention were evaluated as emulsifying agents by their ability to emulsify solvents according to the following procedure:

Three solutions, the first of which contains 6 cc. of water, 4 cc. of [11]Solvesso ®150 and 0.5 g. of the compound which is being evaluated as an emulsifying agent, the second of which contains 6 cc. of water, 4 cc. of perchlorethylene and 0.5 g. of the compound which is being evaluated as an emulsifying agent, and the third of which contains 6 cc. of water, 4 cc. of [12]Varsol No. 1 and 0.5 g. of the compound which is being evaluated as an emulsifying agent, are mixed thoroughly and aged for 1 hour to allow for prewetting equilibrium, after which time the solutions are re-emulsified (by mixing) and 5 ml. of each are run into a [13]Bidwell-Sterling distilling receiver. The amount of separation of the two liquids is then measured at different time intervals; the less the separation, the better the emulsifying ability of the test compound. The results of this evaluation appear in Tables 7, 7A and 7B below.

[11]an alkylated benzene fraction containing 97% aromatics (~70% $C_{10}$ and $C_{11}$ aromatics) and commercially available from Exxon Corp.

[12] a commercially available petroleum hydrocarbon containing approximately 15% aromatics, 0.15% olefins and 85% saturated hydrocarbons.
[13] a commercially available device utilized to measure the separation of two liquids.

TABLE 7

| Test Compound | Separation of Emulsion (ml.), Lower Layer Solvesso® 150 Observation Time, Minutes | | | | | |
|---|---|---|---|---|---|---|
| | 5' | 10' | 15' | 20' | 25' | 30' |
| Ex. 1 | 0 | 0 | 0 | 0 | 0 | 0 |
| Ex. 2 | 0.77 | 1.40 | 1.90 | 2.35 | 2.45 | 2.50 |
| Ex. 3 | 0.40 | 0.75 | 1.10 | 1.40 | 1.70 | 1.95 |
| Ex. 4 | 0 | 0 | 0.10 | 0.20 | 0.35 | 0.50 |
| Ex. 5 | 0.22 | 0.44 | 0.64 | 0.87 | 1.00 | 1.29 |
| Ex. 6 | 0.08 | 0.24 | 0.40 | 0.58 | 0.72 | 0.88 |
| Ex. 7 | 0 | 0 | 0 | 0 | 0 | 0 |
| Ex. 8 | 0.64 | 1.20 | 1.68 | 2.00 | 2.18 | 2.26 |
| Ex. 9 | 0.36 | 0.66 | 0.94 | 1.20 | 1.47 | 1.68 |
| Ex. 10 | 0.11 | 0.11 | 1.30 | 1.86 | 1.96 | 2.05 |
| Ex. 11 | 1.00 | 1.40 | 1.62 | 1.70 | 1.80 | 1.80 |
| Ex. 11b | — | — | — | 1.45 | 1.55 | 1.60 |
| Strodex Super V-8 | 0.30 | 0.52 | 0.80 | 1.00 | 1.25 | 1.50 |
| [14]Tergitol 15-S-9 | 0.16 | 0.39 | 0.70 | 0.96 | 1.50 | 1.30 |
| [15]Gafac RE-410 (pH 6) | 0.16 | 0.26 | 0.40 | 0.50 | 0.60 | 0.70 |
| [15]Gafac RE-610 (pH 6) | 0.16 | 0.26 | 0.40 | 0.50 | 0.60 | 0.70 |
| [15]Gafac RE-610 (acid) | 0.16 | 0.26 | 0.40 | 0.50 | 0.60 0.70 | |

[14] a commercially available condensation product of a linear $C_{13-15}$ secondary alcohol with 9 moles of ethylene oxide.
[15] an alkoxylated monophosphate co-ester available commercially from GAF Corp.

TABLE 7A

| Test Compound | Separation of Emulsion (ml.), Lower Layer Perchlorethylene (a) Observation Time, Minutes | | | | | |
|---|---|---|---|---|---|---|
| | 5' | 10' | 15' | 20' | 25' | 30' |
| Ex. 1 | 0 | 0 | 0 | 0 | 0 | 0 |
| Ex. 2 | 2.00 | >2.50 | >2.50 | >2.50 | >2.50 | >2.50 |
| Ex. 3 | 0.70 | 1.90 | >2.50 | >2.50 | >2.50 | >2.50 |
| Ex. 4 | 0.13 | 0.34 | 0.60 | 0.84 | 1.10 | 1.40 |
| Ex. 5 | 0.70 | 1.80 | >2.50 | >2.50 | >2.50 | >2.50 |
| Ex. 6 | 0.30 | 0.76 | 1.10 | 1.40 | 1.70 | 2.00 |
| Ex. 7 | 0.20 | 0.20 | 0.30 | 0.40 | 0.40 | 0.40 |
| Ex. 8 | 1.50 | 2.92 | >3.00 | >3.00 | >3.00 | >3.00 |
| Ex. 9 | 0.30 | 0.54 | 0.80 | 1.00 | 1.25 | 1.46 |
| Ex. 10 | — | 1.00 | 1.70 | 2.30 | 2.70 | 2.80 |
| Ex. 11 | — | 0.80 | 0.70 | 0.70 | 0.70 | — |
| Ex. 11b | 0.20 | 0.20 | 1.25 | 1.60 | 2.00 | 2.35 |
| Strodex Super V-8 | 0.48 | 0.96 | 1.44 | 1.88 | 2.20 | 2.25 |
| Tergitol 15-S-9 | — | — | 0.86 | 1.08 | 1.24 | 1.42 |
| Gafac RE-410 (pH 6) | 0.30 | 0.50 | 0.80 | 1.15 | 1.30 | 1.60 |
| Gafac RE-610 (pH 6) | 0.30 | 0.50 | 0.80 | 1.15 | 1.30 | 1.60 |
| Gafac Re-610 (acid) | — | 0.46 | 0.70 | 0.90 | 1.10 | 1.30 |

(a) Water separated as top layer due to greater density of perchloroethylene.

TABLE 7B

| Test Compound | Separation of Emulsion (ml.), Lower Layer Varsol No. 1 Observation Time, Minutes | | | | | |
|---|---|---|---|---|---|---|
| | 5' | 10' | 15' | 20' | 25' | 30' |
| Ex. 1 | 0.47 | 0.98 | 1.40 | 1.66 | 1.83 | 1.97 |
| Ex. 2 | 1.40 | 1.91 | 2.10 | >2.10 | >2.10 | >2.10 |
| Ex. 3 | 0.66 | 1.50 | 1.92 | 2.10 | 2.10 | 2.10 |
| Ex. 4 | 0.33 | 0.70 | 1.00 | 1.30 | 1.60 | 1.90 |
| Ex. 5 | 1.70 | 2.20 | >2.20 | >2.20 | >2.20 | >2.20 |
| Ex. 6 | 0.72 | 1.30 | 1.76 | 1.98 | >2.00 | >2.00 |
| Ex. 7 | 0.80 | 1.20 | 1.46 | 1.60 | 1.66 | 1.70 |
| Ex. 8 | 1.10 | 1.60 | 1.80 | 1.90 | 2.00 | 2.04 |
| Ex. 9 | 0.80 | 1.60 | 2.00 | 2.12 | 2.20 | 2.26 |
| Ex. 10 | 1.30 | 2.15 | 2.30 | 2.40 | 2.50 | 2.56 |
| Ex. 11 | 1.40 | 1.76 | 1.93 | 2.02 | 2.06 | 2.10 |
| Ex. 11b | — | 2.02 | 2.22 | 2.34 | 2.40 | >2.40 |
| Strodex Super V-8 | 0.50 | 1.00 | 1.50 | 1.95 | >2.10 | >2.10 |
| Tergitol 15-S-9 | 0.15 | 0.30 | 0.46 | 0.60 | 0.76 | 0.92 |
| Gafac RE-410 (pH 6) | — | 0.14 | 0.25 | 0.35 | 0.44 | 0.55 |
| Gafac RE-610 (pH 6) | — | 0.14 | 0.25 | 0.35 | 0.44 | 0.55 |
| Gafac RE-610 (acid) | 0.50 | 1.00 | 1.30 | 1.60 | 1.80 | 1.90 |

EXAMPLE 20

Several representative compounds of the present invention were evaluated as fiber finishing agents according to the following procedure:

The compound which is being evaluated as a fiber finishing agent is applied to polyester and polyamide filament and staple fiber yarn by the dip/centrifuge method in such a way that the uptake is 0.5% solids in each case. The dynamic yarn/steel friction (sliding friction) on the staple fiber yarn and the yarn/yarn friction (static friction) on the filament yarn is then measured employing a Rothschild "F" meter, which is a widely accepted control friction meter. As regards to the dynamic yarn/metal friction, the unit continuously electronically determines the differences in tension developed in a fiber on yarn by its passage over a pin of the other frictional surface or through a twist of the fiber around a pin. Instrument geometry is carefully controlled allowing internal calculation of "f", the coefficient of friction. With respect to the yarn/yarn friction, the force "p" after the point of friction is expressed as a range representing the reduced tension as a result of the fact that the cohesive forces of the yarn are overcome by the presence of the fiber finishing agent on the yarn (slip) and the tension measured at a point where the cohesive forces of the yarn again dominate (stick). All of the friction measurements are conducted at 20° C. and 65% relative humidity. The results of this evaluation appear in Tables 8 and 8A below

TABLE 8

| | Yarn/yarn friction; Speed - 2 mm/min. Slip-stick friction-"p" | |
|---|---|---|
| Test Compound | Polyester | Polyamide |
| Untreated | 29–46 | 47–58 |
| Ex. 1 | 35–40 | 48–54 |
| Ex. 3 | 34–41 | 44–48 |
| Ex. 4 | 35–43 | 44–45 |
| Ex. 4b | 37–44 | 42–43 |
| Ex. 5 | 31–38 | 26–27 |
| Ex. 6 | 31–36 | 39–43 |
| Ex. 10 | 33–38 | 45–49 |
| Ex. 2 | 36–45 | 49–54 |
| Ex. 2a | 36–43 | 51–57 |
| Ex. 2b | 41–51 | 43–46 |
| Ex. 2c | 39–46 | 50–55 |
| Ex. 2d | 36–39 | 42–47 |
| Ex. 2e | 35–44 | 48–59 |
| Ex. 12 | 36–41 | 49–56 |
| [16]TRYFAC 610-K | 29–38 | 42–48 |
| [17]Sandolube NP | 28–37 | 45–55 |

[16]an alkoxylated monophosphate co-ester available commercially from Emery Industries.
[17]A phosphate ester lubricant available commercially from Sandox, Inc.

TABLE 8A

| | Dynamic yarn/metal friction; coefficient of friction - "f" | | | | | |
|---|---|---|---|---|---|---|
| | Polyester | | | Polyamide | | |
| Test compound | 20 m/min. | 50 m/min. | 100 m/min. | 20 m/min. | 50 m/min. | 100 m/min. |
| Untreated | 0.44 | 0.44 | 0.45 | 0.32 | 0.49 | 0.59 |
| Ex. 1 | 0.65 | 0.58 | 0.60 | 0.46 | 0.59 | 0.63 |
| Ex. 3 | 0.65 | 0.61 | 0.65 | 0.47 | 0.62 | 0.66 |
| Ex. 4 | 0.65 | 0.63 | 0.61 | 0.41 | 0.54 | 0.49 |
| Ex. 4b | 0.65 | 0.58 | 0.60 | 0.39 | 0.54 | 0.54 |
| Ex. 5 | 0.62 | 0.58 | 0.58 | 0.50 | 0.67 | 0.70 |
| Ex. 6 | 0.54 | 0.55 | 0.56 | 0.43 | 0.59 | 0.60 |
| Ex. 10 | 0.55 | 0.59 | 0.60 | 0.52 | 0.69 | 0.67 |
| Ex. 2 | 0.64 | 0.60 | 0.62 | 0.55 | 0.67 | 0.62 |
| Ex. 2a | 0.65 | 0.63 | 0.62 | 0.51 | 0.58 | 0.57 |
| Ex. 2b | 0.53 | 0.66 | 0.65 | 0.57 | 0.54 | 0.54 |
| Ex. 2c | 0.57 | 0.62 | 0.65 | 0.52 | 0.54 | 0.55 |
| Ex. 2d | 0.60 | 0.63 | 0.63 | 0.55 | 0.57 | 0.53 |
| Ex. 2e | 0.56 | 0.63 | 0.62 | 0.52 | 0.53 | 0.57 |
| Ex. 12 | 0.50 | 0.57 | 0.55 | 0.48 | 0.58 | 0.59 |
| TRYFAC 610-K | 0.50 | 0.57 | 0.60 | 0.47 | 0.60 | 0.66 |
| Sandolube NP | 0.47 | 0.52 | 0.55 | 0.45 | 0.54 | 0.60 |

EXAMPLE 21

Several representative compounds of the present invention were evaluated as anti-static agents according to the following procedure:

The compound which is being evaluated as an anti-static agent is applied to polyester and polyamide staple fiber yarn by the dip/centrifuge method in such a way that the uptake is 0.5% solids in each case. The electrostatic behavior is then determined by measuring the discharge halftime in seconds employing a static voltmeter. All of the electrostatic measurements are conducted at 20° C. and at relative humidities of 30% and 65%, respectively. The results of this evaluation appear in Table 9 below.

TABLE 9

| | Discharge half time-seconds; voltage-100V | | | |
|---|---|---|---|---|
| | Polyester | | Polyamide | |
| Test compound | 30% RH | 65% RH | 30% RH | 65% RH |
| Untreated | >180 | >180 | >180 | >180 |
| Ex. 1 | 4 | <1 | >180 | >180 |
| Ex. 3 | 5 | <1 | >180 | 61 |
| Ex. 4 | 4 | <1 | >180 | 74 |
| Ex. 4b | 4 | <1 | >180 | >180 |
| Ex. 5 | .6 | <1 | >180 | >180 |
| Ex. 6 | 2 | <1 | >180 | 77 |
| Ex. 10 | 2 | <1 | >180 | >180 |
| Ex. 2 | 11 | <1 | >180 | >180 |
| Ex. 2a | 29 | >1 | 1300 | 11 |
| Ex. 2b | 1 | >1 | 870 | 38 |
| Ex. 2c | 7 | >1 | 1600 | 115 |
| Ex. 2d | 32 | >1 | 870 | 3 |
| Ex. 2e | 5 | >1 | 810 | 22 |
| Ex. 12 | 700 | 12 | 1740 | 228 |
| TRYFAC 610-K | 3 | <1 | >180 | >180 |
| Sandolube NP | 1 | <1 | >180 | >180 |

The products of Examples 4, 6 and 8-10 are mixtures of compounds having on average the indicated number of —$OC_2H_4$— radicals between the two phosphorus atoms.

What is claimed is:

1. A compound of formula I,

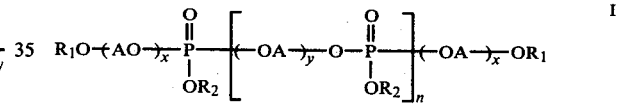

wherein each $R_1$, independently, is the residue of a straight or branched chain $C_6$–$C_{22}$ fatty alcohol or the residue of a mono- or dialkylphenol wherein the alkyl group of the mono- or each alkyl group of the dialkylphenol independently has from 6 to 12 carbon atoms and is straight or branched, each A, independently, is a divalent, aliphatic, straight or branched chain hydrocarbylene group having from 2 to 6 carbon atoms, each x, independently, is an integer 1 to 100, each y, independently, is an integer 2 to 30, n is an integer 1 to 3, and the $R_2$'s have the same significance and are hydrogen or a cation selected from the group consisting of alkali metal, alkaline earth metal, ammonium, mono-, di- and trialkanol ammonium wherein each alkanol group independently has 2 to 4 carbon atoms, mono-, di-, tri- and tetra-alkylammonium wherein each alkyl group independently has 1 to 4 carbon atoms, pyridinium and morpholinium, or a mixture of compounds of formula I.

2. A compound according to claim 1 of formula Ia,

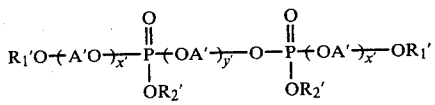

wherein each $R_1'$, independently, is the residue of a straight or branched chain $C_8$-$C_{14}$ fatty alcohol or the residue of a mono- or dialkylphenol wherein the alkyl group of the mono- or each alkyl group of the dialkylphenol independently has from 8 to 12 carbon atoms and is straight or branched, each A', independently, is a straight or branched chain alkylene radical has from 2 to 4 carbon atoms, each x', independently, is an integer 1 to 40, y' is an integer 2 to 20, and the $R_2''$s have the same significance and are hydrogen or a cation selected from the group consisting of alkali metal, ammonium and mono-, di- and trialkanol ammonium wherein each alkanol group independently has 2 to 4 carbon atoms, or a mixture of compounds of formula Ia.

3. A compound according to Claim 2 of formula Ib,

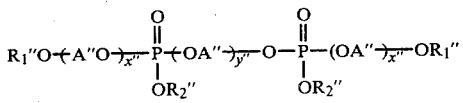

wherein each $R_1''$, independently, is the resdue of a straight or branched chain $C_{10}$-$C_{14}$ fatty alcohol or the residue of a mono-or dialkylphenol wherein the alkyl group of the mono- or each alkyl group of the dialkylphenol independently has from 8 to 10 carbon atoms and is straight or branched, each A'', independently, is ethylene or 1,2-or 1,3-propylene, each x'', independently, is an integer 1 to 20, y'' is an integer 2 to 15, and the $R_2'''$s have the same significance and are hydrogen or a cation selected from sodium, potassium, ammonium or monoalkanol ammonium wherein the alkanol group has 2 to 4 carbon atoms, or a mixture of compounds of formula Ib.

4. A compound or a mixture of compounds according to claim 3 wherein B'' is ethylene and the $+OAB''_{x''}OR_1''$ groups are identical.

5. The compound according to claim 4 having the formula

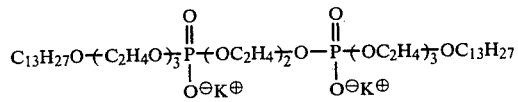

6. A mixture of compounds according to claim 4 having the formula

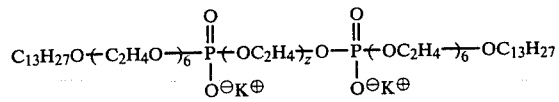

wherein the average value of z is 13.2.

7. A mixture of compounds according to claim 4 having the formula

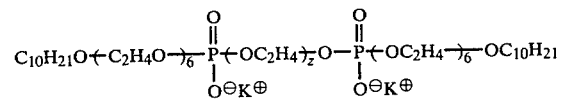

wherein the average value of z is 6.4.

8. A mixture of compounds according to claim 4 having the formula

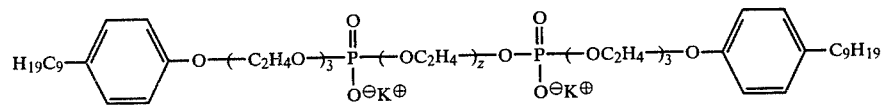

wherein the average value of z is 6.4.

9. A mixture of compounds having the formula

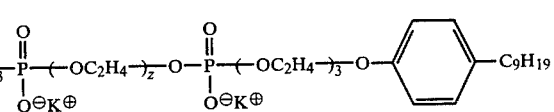

wherein the $R_2''''$'s have the same significance and are sodium, potassium, monoethanol-ammonium, diethanolammonium, diiso-propylammonium or triethanolammonium; and z has an average of 6.4.

10. A mixture of compounds having the formula

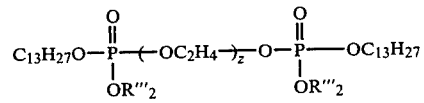

wherein the $R_2''''$'s have the same significance and are hydrogen, potassium, ammonium or monoethanolammonium; and z has an average value of 13.2.

11. A mixture of compounds having the formula

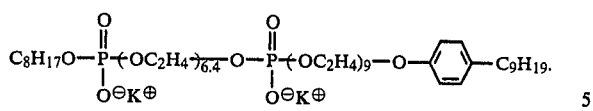
12. The compound of the formula
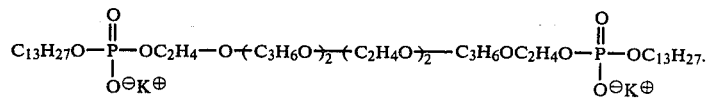

UNITED STATES PATENT AND TRADEMARK OFFICE
CERTIFICATE OF CORRECTION

PATENT NO. : 4,220,611

DATED : September 2, 1980

INVENTOR(S) : Harold P. Wolf

It is certified that error appears in the above—identified patent and that said Letters Patent is hereby corrected as shown below:

Col. 3; delete lines 4-10 in their entirety and substitute therefor

--     12 carbon atoms,
  each A, independently, is a divalent, aliphatic, straight or branched chain hydrocarbylene radical containing from 2 to 6 carbon atoms,
  each x, independently, is 0 or an integer 1 to 100, preferably an integer 1 to 100,
    y  is an integer 2 to 30,
    n  is an integer 1 to 3, and   --.

Col. 3; delete lines 63-65 in their entirety and substitute therefor

--each x", independently, is 0 or an integer 1 to 20,
    y"  is an integer 2 to 15, and
the $R_2$"'s have the same --.

Col. 4, line 62; after "10°" insert -- - 50° --.

Col. 5, line 12; delete the word "to" (second occurrence).

UNITED STATES PATENT AND TRADEMARK OFFICE
CERTIFICATE OF CORRECTION

PATENT NO. : 4,220,611

DATED : September 2, 1980

INVENTOR(S) : Harold P. Wolf

It is certified that error appears in the above—identified patent and that said Letters Patent is hereby corrected as shown below:

Col. 7, line 37; delete "combiined" and insert in its place --combined--.

Col. 10, line 52; delete "decribe" and insert in its place --describe--.

Col. 12, line 1; delete "tetrohydrofuran" and insert in its place --tetrahydrofuran--.

Col. 17, Example 14, line 1; delete "Severl" and insert in its place --Several--.

Col. 20, line 2; delete " 3/4" X 1/4") " and insert in its place -- 3/4" X 6 1/4") --.

Col. 22, under the heading " 25' "; delete "0.70".

Col. 22, under the heading " 30' "; insert --0.70--.

Col. 23, in footnote [17] below TABLE 8; change "Sandox, Inc." to --Sandoz, Inc.--.

UNITED STATES PATENT AND TRADEMARK OFFICE
CERTIFICATE OF CORRECTION

PATENT NO. : 4,220,611

DATED : September 2, 1980

INVENTOR(S) : Harold P. Wolf

It is certified that error appears in the above—identified patent and that said Letters Patent is hereby corrected as shown below:

Claim 2, Col. 25, line 31; after "alkylene", delete "radical has" and insert in its place --group having--.

Claim 4, Col. 26, line 2; delete " B" " and insert in its place --A"--.

Claim 4, Col. 26, line 2; delete "$-(OAB")_{x-}$" and insert in its place -- $-(OA")_{x-}$ --.

Signed and Sealed this

Eleventh Day of May 1982

[SEAL]

Attest:

GERALD J. MOSSINGHOFF

Attesting Officer

Commissioner of Patents and Trademarks